(12) United States Patent
Takahashi et al.

(10) Patent No.: US 7,727,469 B2
(45) Date of Patent: Jun. 1, 2010

(54) AUTOMATIC ANALYZER

(75) Inventors: Katsuaki Takahashi, Hitachinaka (JP); Hiroshi Ohga, Ohmiya (JP); Masaharu Nishida, Hitachinaka (JP)

(73) Assignees: Hitachi High-Technologies Corporation, Tokyo (JP); Hitachi Science Systems, Ltd., Ibaraki (JP)

( * ) Notice: Subject to any disclaimer, the term of this patent is extended or adjusted under 35 U.S.C. 154(b) by 833 days.

(21) Appl. No.: 10/822,663

(22) Filed: Apr. 13, 2004

(65) Prior Publication Data

US 2004/0208787 A1    Oct. 21, 2004

(30) Foreign Application Priority Data

Apr. 16, 2003    (JP)    ............... 2003-110971

(51) Int. Cl.
*G01N 35/00*    (2006.01)
*G01N 35/02*    (2006.01)
*G01N 35/10*    (2006.01)

(52) U.S. Cl. ............... 422/64; 422/63; 422/67; 436/43; 436/45; 436/47; 436/49; 436/50

(58) Field of Classification Search ............. 422/63–67; 436/43, 44, 47–49
See application file for complete search history.

(56) References Cited

U.S. PATENT DOCUMENTS 4,058,367 A * 11/1977 Gilford ................... 422/63

| 5,207,986 | A |   | 5/1993 | Kadota et al. ................... 422/65 |
| 5,209,903 | A | * | 5/1993 | Kanamori et al. .............. 422/65 |
| 5,314,825 | A | * | 5/1994 | Weyrauch et al. .............. 436/43 |
| 5,670,114 | A | * | 9/1997 | Sakazume et al. .............. 422/67 |
| 5,827,479 | A | * | 10/1998 | Yamazaki et al. .............. 422/67 |
| 6,413,475 | B2 | * | 7/2002 | Ishizawa et al. .............. 422/106 |
| 2002/0025275 | A1 |   | 2/2002 | Oonuma et al. ................ 422/64 |
| 2002/0064481 | A1 | * | 5/2002 | Ishizawa et al. ............... 422/64 |
| 2002/0182108 | A1 |   | 12/2002 | Ishihara et al. ................ 422/63 |

FOREIGN PATENT DOCUMENTS

| EP | 1102068 A |   | 5/2001 |
| GB | 2120786 A |   | 7/1983 |
| JP | 63-61165 | * | 3/1988 |
| JP | 03-162672 |   | 7/1991 |
| JP | 3-162672 | * | 7/1991 |
| JP | 6-64070 |   | 8/1994 |
| JP | 10-019899 |   | 1/1998 |
| JP | 10019899 | * | 1/1998 |
| JP | 10-332708 |   | 12/1998 |

* cited by examiner

*Primary Examiner*—P. Kathryn Wright
(74) *Attorney, Agent, or Firm*—Mattingly & Malur, P.C.

(57) ABSTRACT

In an automatic analyzer, when a sample is newly added, all sample barcodes on a sample disk are read. Immediately before dispensing it, second time reading is performed, and the result thereof is checked against that of the first time reading. A sample hand-contact preventing plate is provided above the reading position and dispensing position in order to prevent the sample from being exchanged after the second time reading. This hand-contact preventing plate has a damage-preventing configuration to protect a hand and fingers of an operator against a sampling probe.

6 Claims, 4 Drawing Sheets

AUTOMATIC ANALYZER

BACKGROUND OF THE INVENTION

1. Field of the Invention

The present invention relates to an automatic analyzer that automatically performs a qualitative/quantitative analysis of biological samples such as blood, urine, or the like, and more particularly, to an automatic analyzer capable of preventing the occurrence of a mismatch between a sample and its analysis result due to an interchange of samples by an operator, or the like.

2. Description of the Related Art

In an automatic analyzer that performs a qualitative/quantitative analysis of ingredients of each of samples collected from a plurality of persons, a sample is generally entered into a sample container, and the sample container is set in the automatic analyzer, thereby performing an analysis. Herein, in order to identify whose sample (or what kind of sample [e.g., blood serum, urine, or the like]) is present in a particular sample container, it has been popularized to give an ID using an information recording medium, such as a barcode, to each sample container. This method reduces the occurrence of a mistake such that a person whose particular ingredient has an abnormality is misjudged as having no abnormality due to mixing-up of samples. This method can also save for an operator much time and effort to register sample information at an automatic analyzer on a container-by-container basis. Such a conventional art is disclosed in, for example, Japanese Examined Patent Application Publication No. 6-64070.

SUMMARY OF THE INVENTION

In medical examination centers, hospitals or the like where automatic analyzers are used, because samples to be examined occur intermittently and unpredictably, an operator of automatic analyzer may add or take out samples with respect to the analyzer. In the automatic analyzer set forth in the aforementioned patent document, there is a possibility as follows: even when the ID of a sample is once identified and stored with the mounting position of the sample and the identified sample ID related with each other, if the operator changes the position of the sample thereafter, the sample that was actually subjected to an analysis and the sample that the automatic analyzer recognizes as being so are different from each other.

Accordingly, it is an object of the present invention to provided an automatic analyzer that reduces the occurrence of mismatch between a sample ID once identified and a sample actually measured.

To solve the above-described problem, the present invention provides an automatic analyzer that includes a sample container for holding a sample; a sample dispensing mechanism for dispensing a sample in the sample container; a sample container transfer mechanism for transferring the sample container to the sample dispensing position in the sample dispensing mechanism; a reaction vessel where the sample dispensed by the sample dispensing mechanism is discharged and mixed with a reagent; and a measuring mechanism for measuring a reaction in the reaction vessel. In this automatic analyzer, an information recording medium on which information for identifying a sample in the sample container is recorded, is attached to the sample container. This automatic analyzer further includes the mechanisms of: reading the information recorded on the information recording medium and identifying the sample in the sample container, prior to the dispensation of a sample by the sample dispensing mechanism; thereafter, reading again the information recorded on the information recording medium attached to the sample container, immediately before or immediately after the dispensation of the sample by the sample dispensing mechanism, and thereby performing identification of the sample in the sample container; and identifying whether the sample that has been identified immediately before or immediately after the dispensing is the same as a sample that is about to be dispensed or a sample that has been dispensed.

DESCRIPTION OF THE PREFERRED EMBODIMENTS

Figure 1:
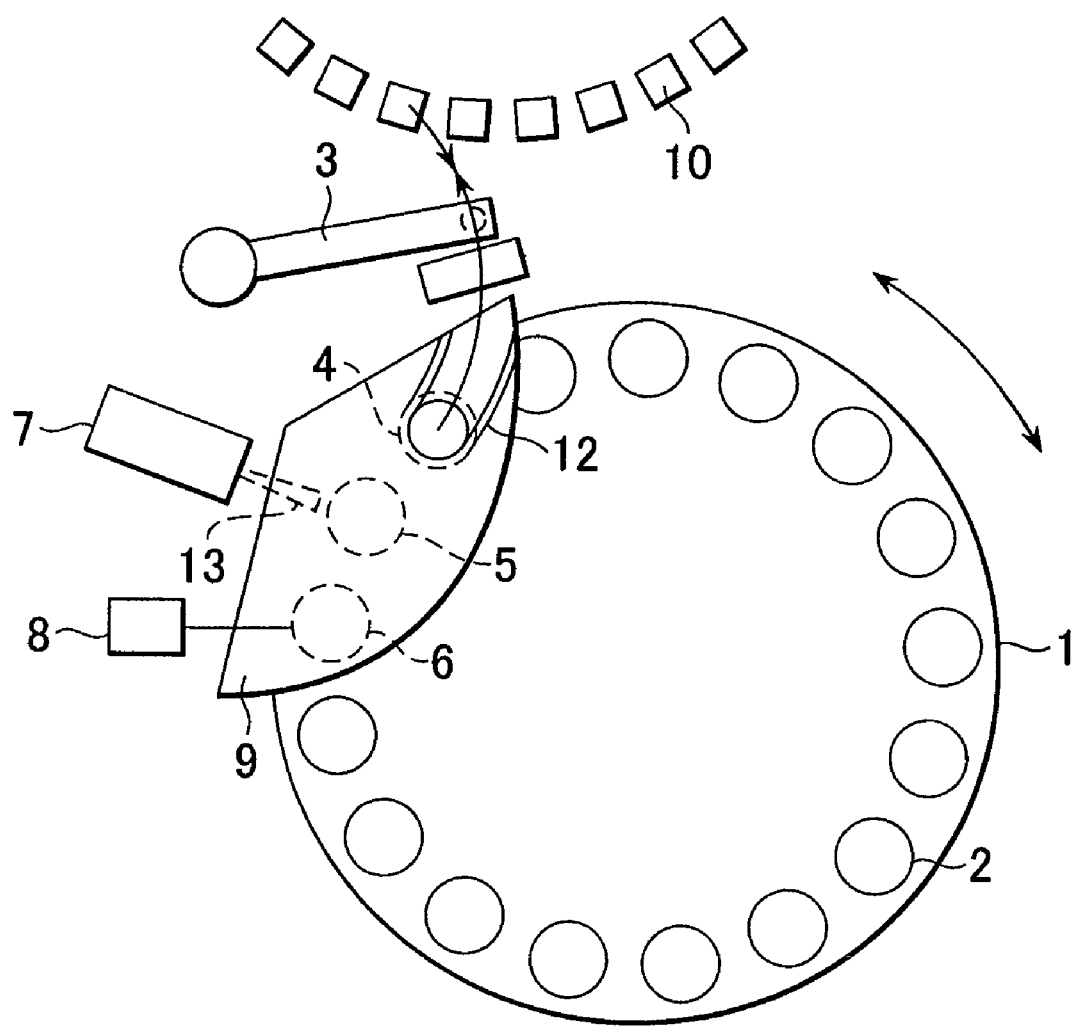
FIG. 1 is a plan view showing the vicinity of a sample disk according to the present invention.

Samplers for an automatic analyzer (here, the "sampler" refers to a mechanism for transferring a sample container containing a sample to a sample dispensing position) are broadly divided into a disk sampler type and a rack sampler type. First, the present invention will be described taking the disk sampler type as an example.

In the disk sampler type, a plurality of sample containers are arranged on a circular disk, and it suffices only to rotate the disk up to a sample dispensing position, thereby simplifying the structure of a drive mechanism. Also, because an automatic reexamination can be performed with a sample mounted on the disk, there is no need for a special mechanism, so that the disk sampler type is used for automatic analyzers of a small size and intermediate size. In general, when attempting to add a sample in course of making analysis by a disk sampler type, its operation becomes disadvantageously cumbersome and difficult to perform. When there are vacant positions on the sample disk, it is necessary for the operator to place samples in the vacant positions and additionally input corresponding position numbers from an operation screen on a sample-by-sample basis (or it is necessary to input information that samples were added from what position number to what position number). This is because, in a sampling stop situation in which the apparatus has finished dispensing all samples on the disk and is awaiting analysis results for a reexamination, the apparatus recognizes that there are no more new samples, so that it is necessary to notify again the apparatus of the situation and resume the dispensing. When there are vacant positions, the operation is rather easy to perform. However, when the disk becomes full of samples, i.e., there is no vacant position, the disk rotates sometimes and its stop position changes, although it is displayed on the screen which samples have already been subjected to analyses (including reexaminations) or not. As a result, the interchanging operation between samples while searching for the position of a sample to be taken out puts a mental burden upon the operator. Furthermore, once the operator has erroneously exchanged a sample after reading its sample identification information, this results in that the operator has made the serious mistake of doing an analysis with samples mixed up. Therefore, in much fear of mixing-up of samples, some operators perform an analysis by batch processing on a disk-by-disk basis in the case of a disk sampler type. That there is fear of mixing-up of samples to such an extent that they do so would become a large psychological burden upon them.

After additional samples are placed on the disk during analysis, first time reading of many sample identification-label information is performed while rotating the sample disk upon receipt of an instruction input from the operator. Based on this first information, an item inquiry is made at a host computer. This item inquiry is about what items are to be analyzed for a particular sample. Many of large hospitals and medical examination centers that use in combination a plurality of automatic analyzers, employ such a host computer in order to collectively manage data. However, when using a single automatic analyzer on a standalone basis, such an inquiry is not necessary, but it suffices only to store information read in advance, in an information storage section. The item inquiry at the host computer must be made at least about 50 seconds before dispensing, because an analysis section requires preparation time, and the apparatus is given a measure of time for receiving an answer from the host computer. In other words, it is necessary that the reading of barcodes has been completed 50 seconds before dispensing (preceding reading).

In the present invention, after about 50 seconds have elapsed, immediately (about 4 seconds) before the sampling probe starts dispensing, second time reading of identification-label information of a sample to be dispensed is performed. The second time reading is adapted to be conducted on a sample-by-sample basis. The results of first time and second time reading are checked against each other. This arrangement makes it possible to confirm that the sample actually dispensed and the sample preliminarily stored are identical, thereby eliminating the mixing-up of samples. If information on the sample preliminarily stored and information on the sample read before dispensing are different from each other, the analysis result can be brought into correspondence with the information on the sample read before dispensing. When the information on the sample read at the second time and the information on the sample that is read at the first time and stored in advance are different from each other, a function of issuing an alarm to the operator of the apparatus, and/or a function of stopping the analysis operation of the apparatus may be additionally provided.

The second time reading may be performed immediately after dispensing. In this case, although the preliminary alarming to the operator and stoppage of analysis operation cannot be done, it is confirmed that the sample actually analyzed is really identical to the sample preliminarily recorded. This enhances the reliability of analysis results.

It is preferable to provide a sample hand-contact preventing plate (cover) in order to prevent a sample container from being exchanged by the operator either until the pertinent sample is dispensed after completing the second time reading, or until the second time reading is completed after dispensing the pertinent sample.

This is because, even if the second time reading is performed with considerable effort, if the apparatus is configured to allow the operator to exchange the sample container during a dispensing operation before or after the second time reading, the effectiveness of the present invention will be reduced. Providing the above-described sample hand-contact preventing mechanism would prevent a malfunction due to the interchange of samples by the operator, and in addition, even if, in the first time reading, an sample ID is erroneously read (due to a malfunction of an information reading mechanism), providing the above-described mechanism would produce the effect of being capable of correcting the error. Specifically, when the first time reading result and second time reading result are different from each other, urging the operator to exert caution by issuing an alarm makes it possible to determine whether the mismatch is attributable to the interchange of samples by the operator or a malfunction of the information reading section.

A sample container presence/absence detector may be provided to perform container presence/absence detection while performing the first time reading of the sample identification-label information while rotating the sample disk. Since this container presence/absence detection is performed while rotating the sample disk, the output of its detection signals vary in accordance with relative positions of containers depending on reflection conditions of light. That is, the detection signals become wavy. It is also preferable that this detector can capture peaks of the reflection signals at the time when containers are present, by latching the detected signals so as to reliably detect the signals. Only for positions about which reading of sample identification-label information failed in the first time reading while rotating the disk although containers were set there, a reading operation with respect to identification information is performed again. Herein, the rotational speed of the sample disk during the aforementioned rereading is made lower than that during the first time reading operation, whereby the read rate of sample identification information can be improved.

It is preferable that the above-described sample hand-contact preventing plate be configured to have a protective function of preventing the front end of the sampling probe from injuring the operator.

More specifically, the sample hand-contact preventing plate is preferably arranged as follows: when pushed by hand of the operator, the sample hand-contact preventing plate retreats from on the sample disk; it has a detector for detecting that it has retreated; and when its retreat detection function comes into play, the moving operation of the sampling probe is inhibited in order to protect a hand and fingers of the operator from being injured by the sampling probe.

On the other hand, the rack sampler type is an automatic analyzer of type in which a plurality of analysis units are connected to each other by a conveying line and in which the conveying line conveys sample racks supplied to a rack supply section, to intended analysis units. The rack sampler type analyzer dispenses samples in intended individual analysis units, and thereafter collects the samples by another analysis unit or a sample rack collecting section via the conveying line.

Typically, the automatic analyzer system of rack sampler type has a mechanism in which, before introducing a sample rack mounting a plurality of (about five) sample containers thereon into the conveying line, information recording medium attached to the sample rack is read to identify the ID of the rack, and in which, based on the identified information, it is determined to which analysis unit the sample rack is to be conveyed. In this case, the ID of the sample rack and the ID of the sample container mounted on the sample rack are stored in the system in a state where they are related to each other. Even with such a rack sampler type, if an interchange of sample containers is made in the sample rack on the conveying line, the matching between the rack ID and the sample ID cannot be achieved. Nevertheless, even in such a system, after the ID reading for registering the sample rack ID or sample container ID at the host computer, ID identification of the sample container or sample rack is performed immediately before or immediately after dispensing the sample, thereby enabling a mistake due to a malfunction of the ID reading section or an interchange of samples by the operator to be effectively prevented.

Hereinafter, embodiments according to the present invention will be described with reference the accompanying drawings.

Figure 2:
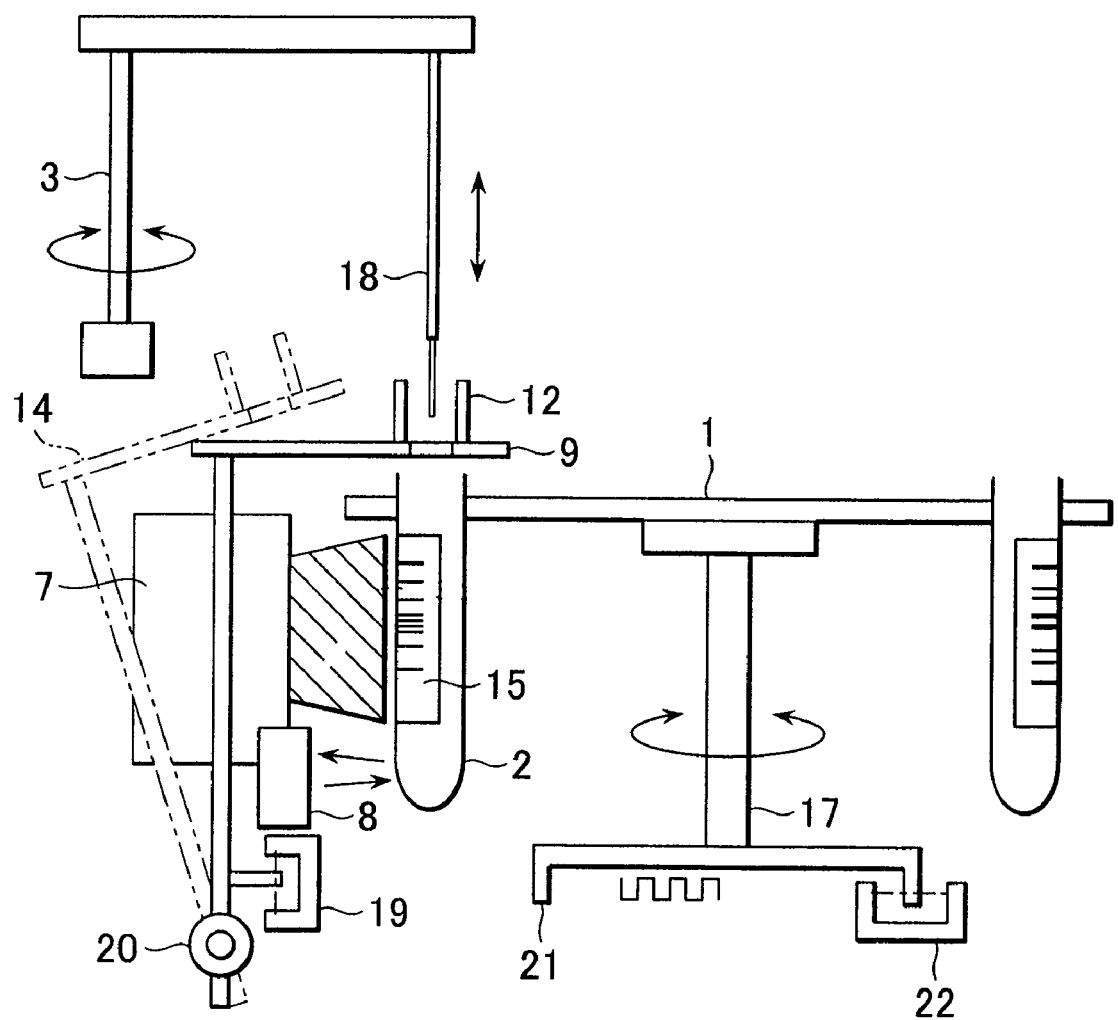
FIG. 2 is a front view showing the vicinity of the sample disk according to the present invention.

An embodiment according to the present invention is shown in FIGS. 1 and 2. FIGS. 1 and 2, respectively, are plan view and front view of arrangements in the vicinity of a sample disk according to the present invention.

Sample containers 2 are set in a sample disk 1 having a plurality of holes for holding many sample containers. A sample identification-label 15 (barcode label) is attached to each sample container. A reader 7 (barcode reader) for the sample identification-label 15 is provided on the side of the sample disk so that barcodes attached to the sample containers can be read while rotating the sample disk. Because a recent barcode reader is capable of high speed reading, it can instantaneously read many sample labels while they are passing a read zone 13, without the need to stop the disk on a sample-by-sample basis.

Even by rotating the sample disk on which 50 samples can be mounted on the circumference thereof, at the rotational speed of about 5 seconds per round, it is sufficiently possible to read 50 samples.

A sample container presence/absence detector 8 (light reflection type sensor) was newly provided. While performing first time reading of many sample identification-label information while rotating the sample disk, container presence/absence detection was instantaneously performed on a simultaneous basis. Checking of success/failure in reading of sample identification-label information and container presence/absence checking are performed. For positions about which the reading of information failed because containers were not set there, an alarm of reading failure is prevented from being issued (it is natural that the reading of information fails because of the absence of container).

A reading operation with respect to identification information is performed again only for positions about which reading of sample identification-label information failed (this failure is due to some scratch of barcode-labels, their being soiled, or the like) although containers were set there. The rotational speed of the sample disk during the time when the positions about which the reading of the information has failed cross over a read zone 13, is made lower than the rotational speed during the first time reading operation, thereby enhancing the reading success rate of the sample identification information. Crossing over the read zone at a low speed would allow the scan time number (retry number) of the reader to increase, resulting in an increased reading success rate.

Positions about which reading of information has been successfully performed are arranged to cross over the read zone at a high speed, thereby reducing rereading time.

The sampling mechanism 3 actuates a sampling probe 18 to dispense a sample in a sample container, in a reaction vessel 10. The position 5 where the reading of sample identification-label is to be performed, and the position 4 where the sampling probe is inserted in the vessel to dispense a sample were provided with a sample hand-contact preventing plate 9. After placing additional samples on the sample disk during analysis, based on an instruction input (sample disk scan) of the operator, first time reading of sample identification-label information of all samples is performed while rotating the sample disk. This reading is instantaneously performed while all samples are crossing over the read zone 13 without the need to stop the disk on a sample-by-sample basis. Comparison of information before and after the disk scan allows the operator to know which are newly added ones. Also, when the position where a sample was mounted earlier on the disk has been merely changed to another position, the sample can be subjected to an analysis as being in a new position. Moreover, even when a sample not to be take out, such as a sample waiting for reexamination, is erroneously taken out, that error can be detected immediately after disk scanning to thereby issue an alarm. Such safety protection equipment from the apparatus part offers to the operator an advantage in that he/she can perform operations with peace of mind.

Based on this first time information, an item inquiry regarding a new additional sample (inquiry as to which items are to be analyzed for this new sample) is made at the host computer. This item inquiry at the host computer must be made about 50 seconds before sampling because the analysis section requires preparation time. After about 50 seconds have elapsed, immediately (4 seconds) before the sampling probe starts dispensing, one sample that was about to be dispensed was moved in front of the reader, and second time reading of identification-label information was performed. Herein, the results of the first time and second time reading by sample disk scanning were checked against each other. If samples are interchanged during the time period from the point in time when the reading by the sample disk scanning has been completed to the time to perform sampling, there is a risk of causing mixing-up of samples. However, checking the results of the first time and second time reading against each other in the present invention completely eliminates this risk. Samples of which the first and second checking results have mutually matched are exclusively shifted to respective dispensing operations. After the second time reading has been completed, the pertinent sample containers are maintained under the sample hand-contact preventing plate until the sampling is completed, and therefore, the access from the operator to the pertinent samples is impossible, thereby perfectly preventing mixing-up of samples due to a misoperation.

Figure 3:
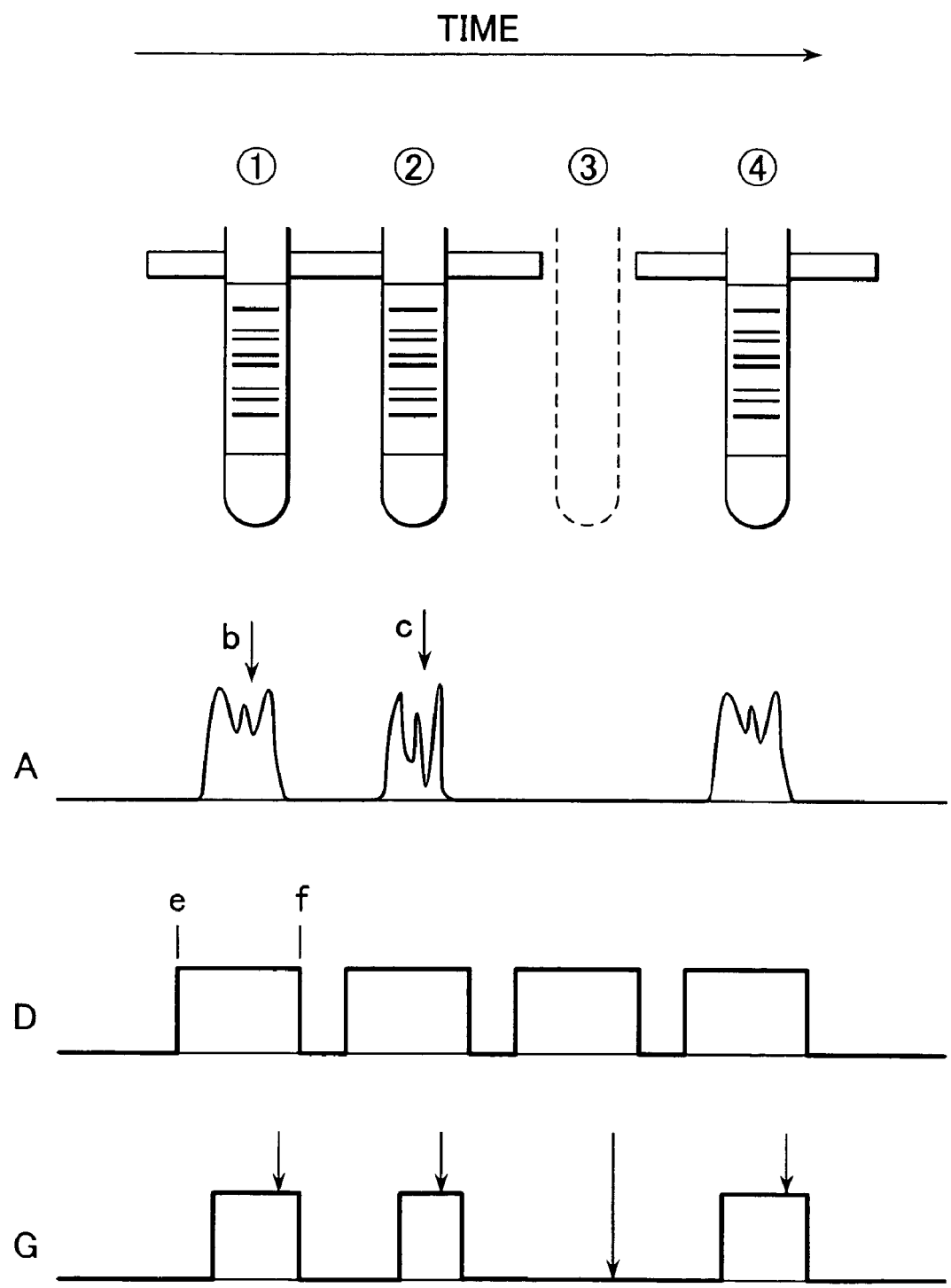
FIG. 3 is a diagram explaining latch processing with respect to presence/absence detecting signals for a sample container.

As described-above, a sample container presence/absence detector 8 is provided, and while performing first time reading of many sample identification-label information while rotating the sample disk, container presence/absence detection is concurrently performed. Since this container presence/absence detection is performed while rotating the sample disk, the output of its detection signals vary in accordance with reflection conditions of light or relative positions of containers. This is a portion with which we have troubles in the type in which a status is viewed with the disk stopped. That is, the detection signals are wavy as observed while moving the disk. This detector is arranged to capture peaks of the reflection signals at the time when containers are present, by latching the detected signal so as to reliably detect the signals. As shown in FIG. 2, a rotation detecting plate 21 is provided below a disk drive section 17, and detects, by a detector 22, grooves corresponding to the sample mounting holes, the grooves being provided in the detecting plate. Here, latch processing method for signals will be described with reference to FIG. 3. Three samples are mounted in the positions (1), (2), and (4), and the position (3) is vacant. When rotating the disk under this situation, raw signals of the container presence/absence detector 8 appear with large waviness. This is because reflection conditions are different depending on a position since the containers have a round shape. If a status check is simply performed at the time of "b" or "c", the case of "c" is misjudged to be devoid of a container. "D" shows signals of the detector 22 due to the grooves in the rotation detecting plate 21. Based on these signals, performing a latch-start at the time "e" and performing a latch release at the time "f" allows the signal A to regenerate as the signal G. Checking on the signal G at the times indicated by the arrows enables a reliable container presence/absence detection.

The sampling probe 18 is dangerous because the front end thereof is sharp like a needle. Since the sampling probe 18 moves on the sampling disk and descends in the sample container, the access to the sample disk during analysis involves a danger.

As shown in FIGS. 1 and 2, the sample hand-contact preventing plate 9 has longitudinal walls 12, and the front end of the sampling probe remains hidden in the longitudinal walls on its moving locus. Thus, the sample hand-contact preventing plate 9 is configured to have a protection mechanism to prevent injury to the operator.

The sample hand-contact preventing plate 9 is configured so as to retreat from on the sample disk when pushed by hand of the operator, and it can retreat by falling around a fulcrum 20, as shown by a retreating position 14. The sample hand-contact preventing plate 9 has a detector 19 for detecting that the sample hand-contact preventing plate 9 has retreated. When the retreat detection function of the detector 19 comes into play, the moving operation of the sampling disk is inhibited to protect a hand and fingers of the operator from being injured by the sampling probe, and to prevent the probe from being bent by its collision against the sample hand-contact preventing plate 9. This retreating function is needed when the sample disk is removed or set with respect to the apparatus in its entirety, as well. When the sample disk is to be rotated, such a method is used in which, a rotation warning light (not shown) blinks several seconds earlier to give advance notice of a danger. Even if, in the process of the operator's accessing to the sample disk for newly adding a sample without noting the blink, the disk should start rotating and the operator's hand should be carried into the disk to thereby collide against the sample hand-contact preventing plate 9, there would be very little risk of injuring the hand. This is because the hand-contact preventing plate 9 has a streamlined shape as shown in FIG. 1, and also it can be retreated by a weak force. Also, in the case of the sampling probe for a capacitive liquid level sensor, by making the hand-contact preventing plate 9 using an electrically conductive material and grounding it, it can perform the function of protecting the sampling probe against external electrostatic noises, and also serves to prevent a malfunction of the liquid level sensor.

Figure 4:
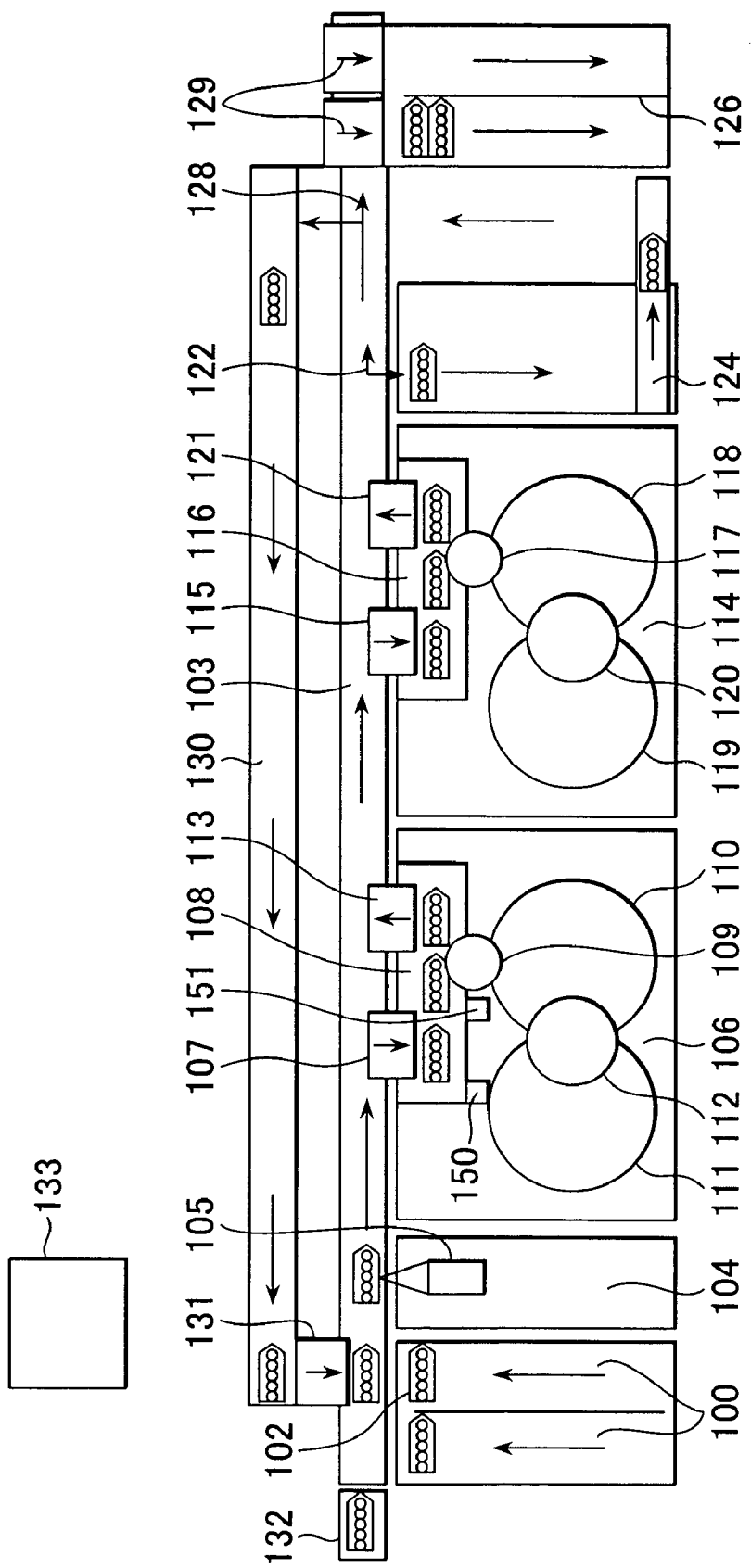
FIG. 4 shows an example of a rack sampler type automatic analyzer into which the present invention has been incorporated.

FIG. 4 shows an example of a rack sampler type automatic analyzer in which the present invention has been incorporated. A sample rack 102 mounting five sample containers is set in a rack supply section 100, and conveyed via a conveying line 103 to analyzers 106 and 114. First, in order to read information recorded on the information recording medium attached to the sample rack 102, the sample rack 102 carried on the conveying line 103 has information recorded on its information recording medium read by a barcode reader 105, and based on the information, a computer 133 for control determines which analysis unit is to be used to analyze the sample. If the analysis is performed using the analyzer 106, a rack is pulled in from a rack pulling-in section 107 to a rack pulling-in line 108. Prior to dispensing of a sample from a sample container on a rack using the dispensing mechanism 109, the information of the sample rack is read by a first rack information reading mechanism (barcode reader) 150. The reading result by the first rack information reading mechanism is sent to a host computer (not shown) via the computer for control, and collation of data is performed there. Then, immediately before the dispensing by the dispensing mechanism 109, the rack information is again read by a second rack information reading mechanism (barcode reader) 151, and this result is checked against that of the first time rack information reading. That is, it is checked whether there was any interchange of samples by the operator between the first rack information reading (involving checking of sample data with the host computer) and the second rack information reading, or whether any error was found in the result of first rack information reading, namely, double checking is performed. Of course, the second rack information reading may be performed immediately after dispensing.

In FIG. 4, the rack information reading mechanism on the analysis unit 114 is omitted from illustration, but it has a reading mechanism similar to the above-described rack information reading-mechanism on the analysis unit 106.

The sample rack subjected to dispensing in the analysis unit 106 is pulled back to the rack conveying line 103 by the rack pulling-back mechanism 113 of the pulling-in line 108. Here, reference numeral 110 denotes a sample disk for mounting sample containers for temporarily storing samples, numeral 111 denotes a reagent disk for storing a reagent that is mixed and allowed to act with a sample, and numeral 112 denotes a reaction disk for mounting a reaction vessel in which the sample and reagent are allowed to act with each other. Because the analysis unit 114 has a similar structure, descriptions thereof using reference numerals are omitted.

The sample rack that has been subjected to an analysis in each of the analysis units waits for analysis result on a buffer line 124. Thereafter, the sample rack is collected into a collecting section 126 via a rack transfer mechanism 129, or when it is determined that a reexamination is necessary because some problem has been found in the analysis result, the sample rack is returned to the vicinity of the rack supply section 100 by the rack pulling-back line 130 via a rack allocation mechanism 128, and then returned to the conveying line 103 via a rack transfer mechanism 131.

According to the present invention, since it is possible to eliminate the risk of sample mixing-up due to misoperation, mental burden upon the operator can be extremely reduced. When attempting to newly adding samples, it suffices only to mount the samples and provide a disk scan instruction. Because sample identification reading is implementable in a short time, the operator has only to operate for a short time, and can leave the apparatus to do another work. Furthermore, the sample hand-contact preventing plate according to the present invention can protect the operator from injury to his/her hand and fingers, and performs the function of protecting the sampling probe against external electrostatic noises, as well as serves to prevent a malfunction of the liquid level sensor.

What is claimed is:

1. An automatic analyzer comprising:
a sample dispensing mechanism that dispenses a sample from a sample container;
a sample container disk, arranged to accommodate a plurality of sample containers, including said sample container, arranged circularly on said sample container disk, and rotated to transfer the sample containers to a sample dispensing position of said sample dispensing mechanism;
reaction vessels in which samples dispensed by said sample dispensing mechanism are discharged;
a measuring unit that measures reactions in said reaction vessels;
an information recording medium attached to said sample container, that stores information for identifying a sample in said sample container;

an information reader arranged to read, when said sample container is positioned at an information reading position, sample information recorded on said information recording medium attached to said sample container positioned at said information reading position;

an information storing section that stores said read sample information;

a controller that controls said information reader to perform said reading of said sample information recorded in said information recording medium prior to a first sample dispensing operation of said sample dispensing mechanism, identifies, and stores said sample information in said information storage section, said controller controls said information reader to again perform said reading and identification of said sample information recorded in said information recording medium just before a second sample dispensing operation of said sample dispensing mechanism, wherein said controller further checks said stored sample information to determine whether or not the sample to be dispensed by said sample dispensing mechanism in the second sample dispensing operation is the same sample whose information has been previously read by said information reader prior to said first sample dispensing operation, wherein said controller controls said sample dispensing mechanism to dispense a sample from said sample container when the sample to be dispensed is determined to be the same sample whose information has been already read by said information reader; and further comprising a cover configured to prevent a sample container from being taken out of the sample container disk from the time said information reader again performs said reading of information recorded in said information recording medium until after said second sample dispensing operation of said sample dispensing mechanism.

2. An automatic analyzer according to claim 1, wherein said controller issues an alarm when a sample that has been dispensed is different from the sample identified by the information previously read by said information reader.

3. An automatic analyzer according to claim 1, wherein the cover comprises a portion covering at least one part of the front end of a probe of the sample dispensing mechanism on a moving locus of the probe.

4. An automatic analyzer according to claim 1, wherein the cover further comprises a mechanism for moving from a position covering the sample container disk so that a sample container on the sample container disk can be taken out.

5. An automatic analyzer according to claim 4, further comprising a movement detector for detecting the movement of the cover, wherein said controller controls said sample dispensing mechanism so as not to dispense a sample when the movement detector detects the movement of the cover.

6. An automatic analyzer according to claim 1, wherein the cover is made of an electrically conductive material.

* * * * *